United States Patent [19]

Guanti et al.

[11] Patent Number: 5,254,681
[45] Date of Patent: Oct. 19, 1993

[54] PROCESS FOR PREPARING MONOBACTAMES AND THEIR INTERMEDIATE PRODUCT

[75] Inventors: Giuseppe Guanti; Luca Banfi; Enrica Narisano; Giorgio Cevasco, all of Genova, Italy

[73] Assignee: Consiglio Nazionale Delle Ricerche, Rome, Italy

[21] Appl. No.: 884,226

[22] Filed: May 11, 1993

Related U.S. Application Data

[63] Continuation of Ser. No. 562,028, Aug. 2, 1990, abandoned.

[30] Foreign Application Priority Data

Aug. 2, 1989 [IT] Italy .................. 21426 A/89

[51] Int. Cl.$^5$ .................. C07D 201/08
[52] U.S. Cl. .................. 540/355
[58] Field of Search .................. 540/355

[56] References Cited

PUBLICATIONS

Comprehensive in Organic Chemistry, vol. 2 p. 928.
Journal of Organic Chemistry vol. 47, 5160–67 1982.
Tetrahedron, p. 5553 (1988).
Gutsche et al., (1975) *Fundamentals of Organic Chemistry*, Prentice-Hall, Inc. Englewood Cliffs, N.J., pp. 96–97 and 507–513.
Cimarusti et al, Med. Res. Reviews, vol. 4, No. 1, 1–24 (1984).
Cimarusti, Journal of Medicinal Chem., vol. 27, No. 3, Mar. 1984.
Cimarusti et al, Chemistry in Britain, Apr. 1983.
Floyd et al, J. Org. Chem. 1982, 47, 5160–5167.
Elliott, J. Chem. Soc., 1950 pp. 62–68.
Guanti et al, Tetrahedron, vol. 44, No. 17, pp. 5553–5562.
Sykes et al, Nature, vol. 291, Jun. 11, 1981.
Imada et al, Nature, vol. 289, Feb. 12, 1981.
Cimarusti et al, Tetrahedron, vol. 39, No. 15, pp. 2577–2589, 1983.

*Primary Examiner*—Thurman K. Page
*Assistant Examiner*—Jyothsna Venkat
*Attorney, Agent, or Firm*—Birch, Stewart, Kolasch & Birch

[57] ABSTRACT

There is described a process for preparing monobactames of formula:

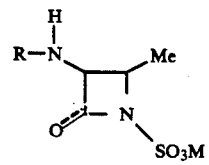

where R=acyl, and their pharmaceutically acceptable salts, starting from ethyl (S)-3-hydroxybutanoate through the reaction intermediate (3S, 4R)-3-hydrazino-4-methyl-2-oxo-1-azetidine sulfonic acid or a salt thereof. This intermediate is new and therefore represents a further object of the present invention.

14 Claims, No Drawings

PROCESS FOR PREPARING MONOBACTAMES AND THEIR INTERMEDIATE PRODUCT

This application is a continuation of application Ser. No. 07/562,028 filed on Aug. 2, 1990, now abandoned.

FIELD OF THE INVENTION

The present invention relates to a new process for the synthesis of monobactames of formula (1)

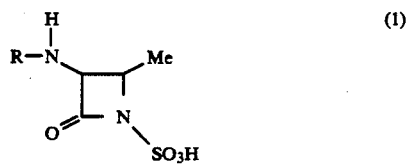

where R=acyl
and their pharmaceutically acceptable salts, starting from ethyl (S)-3-hydroxybutanoate, and to the intermediate of formula (10) which is useful for carrying out said process:

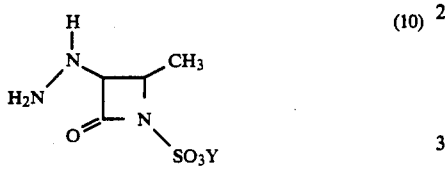

PRIOR ART

The discovery of substances having antibacterial activity (referred to as monobactames or sulfazecines) and characterized by a 2-azetidinone backbone exhibiting an acylamine group in position 3 and a sulfonic acid group in position 1 [R. B. Sykes et al. Nature 291, page 489, (1981); A. Imada et al. Nature 291, page 590 (1981)] has opened a broad research field and several non-natural derivatives of this class have been successively prepared by synthesis. In particular, the monobactames of formula (1). and their pharmaceutically acceptable salts, exhibit a marked antibiotic activity, which renders them particularly interesting for pharmacological purposes.

[See Med. Res. Rev. 4.p.1–24 (1984); Tetrahedron, 2577 (1983); J. Med. Chem. Vol. 27, N° 3, p. 247–53 (1984); Chemistry in Britain, April 1983, p. 302–303; J. Org. Chem. Vol. 47, N° 26, p. 5160–5167 (1982)]. Such 4-substituted monobactames, however, cannot be prepared microbiologically, wherefore a fully enantiospecific synthesis is necessary to prepare them. Furthermore it was proved that the cis-4-methyl monobactames are even more active and resistant to β-lactamases than their trans analogous. Such compounds were prepared by acylation of zwitterion (11), the preparation of which, starting from L-allotreonine, is described in J. Org. Chem. Vol. 47 No. 26, pages 5160–5167 (1982) [see also NL-A-8100571]. However, it is known that L-allotreonine is a product difficult to obtain, as it requires a synthesis in several steps [see also J. Chem. Soc., 62 (1950)].

An object of the present invention is a new fully synthetic process carried out starting from ethyl (S)-3-hydroxybutanoate (a product easily obtainable by microbiological or catalytic reduction of ethyl acetoacetate), which leads to the preparation of products of formula (1) and salts thereof, having a correct relative and absolute configuration, in a simple manner, realizable on an industrial scale without any difficulty. The compounds of formula (1) can be obtained, as already explained, also in the form of pharmacologically acceptable organic or inorganic salts. Examples of organic salts are the salts with amines, such as for example trimethylamine or triethylamine, or quaternary ammonium salts, such as the tetra-n-butylammonium salts. The examples of inorganic salts include salts of alkali-metals such as lithium, sodium, potassium and salts of alkaline earth metals, such as calcium and magnesium.

DETAIL DESCRIPTION OF THE INVENTION

The new process according to the present invention is represented by

SCHEME 1

$R^1$=alkyl, acetyl, benzyl

Y=H, Na, Li, K, Mg, Ca, trimetylammonium, triethylammonium, tetra-n-butylammonium R=acyl, preferably having the configuration (3S,4R)

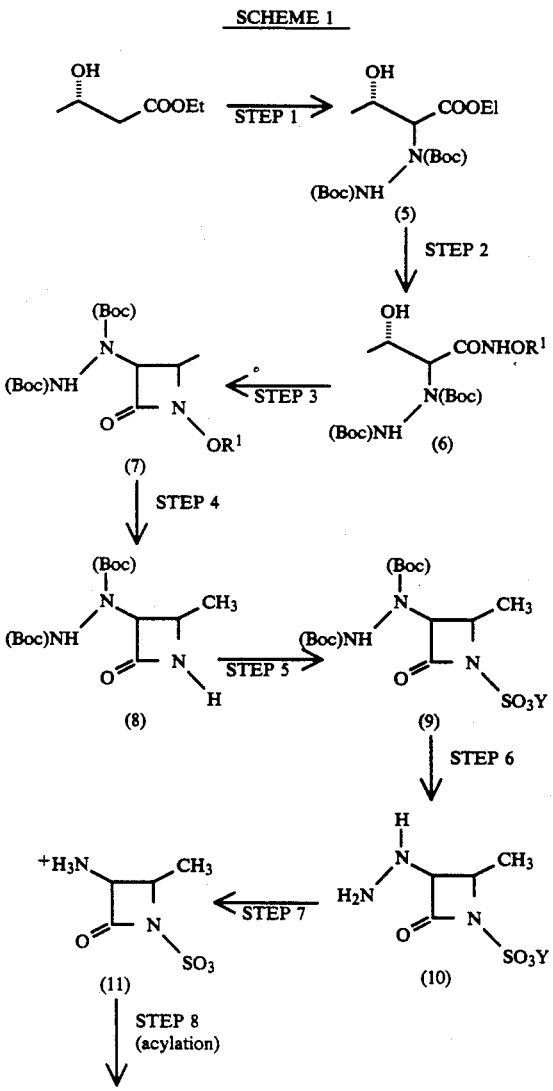

-continued
SCHEME 1

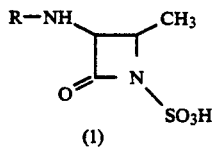
(1)

As shown in the scheme, zwitterion (11), which is a key intermediate for obtaining, through an acylation reaction, any 4-methyl monobactame having relative "cis" configuration, was obtained starting from ethyl (S)-3-hydroxybutanoate (4) through the intermediate ethyl (2S,3S)-2-[N,N'-bis-tert.butyloxycarbonyl)-hydrazino]-3-hydroxybutanoate (5). The conversion of (4) into (5) was already described in Tetrahedron, page 5553 (1988). The (2S,3S)-2-N,N -bis-(tert-butyloxycarbonyl)hydrazino-3-hydroxybutanehydroxamates (6) [where $R^1=C_{1-3}$ alkyl (for example methyl, ethyl, propyl) benzyl or acetyl] are preparable from (5) in two steps. The first step consists in the basic hydrolysis of the ester group. That can be carried out for example by means of a treatment with an excess of a solution between 0.1 and 2 N of basic hydroxides such as lithium hydroxide, sodium hydroxide, potassium hydroxide, etc. in water, in the presence or in the absence of one or more water-soluble organic co-solvents such as methanol, ethanol, tetrahydrofuran, dioxane, dimethylformide, acetonitrile, etc., or in an alcoholic solvent such as methanol or ethanol. The product thus obtained can be isolated in the form of a salt or in the form of free carboxylic acid (after acidification) by using conventional separation methods such as extraction, chromatography or crystallization. As an alternative, the carboxylate solution can be directly utilized for the successive reaction.

The second step consists in the reaction with the suitable 0-substituted hydroxylamine (or with a hydroxylammonium salt thereof). Said reaction is carried out starting from a solution resulting from the preceding reaction, after acidification to pH values ranging from 3 to 8 (or starting from the carboxylic acid or from a salt thereof, previously purified, dissolved in an analogous solvent mixture at an equal pH value), by addition of the proper 0-substituted hydroxylamine (for example 1-2 equivalents) or of a hydroxylammonium salt thereof and of a condensing agent such as e.g. N,N'-dicyclohexylcarbodiimide (DCC) or 1-(3-diaminopropyl)-3-ethylcarbodiimide (WSC) (for example 2 equivalents); excellent yields are obtained for example for $R^1$=benzyl, making use of tetrahydrofuran as a co-solvent and of WSC as a condensing agent and operating at a pH from 4 to 5.

Product (6) ($R^1$=methyl) was obtained by using 1-(3-diamino-propyl)-3-ethylcarbodiimide as a condensing agent and by operating at a pH from 4 to 5.

Product (6) ($R^1$=acetyl), conversely, was obtained by treating (5) with hydroxylamine in an alcoholic solution, which was made basic by the presence of hydroxides such as e.g. lithium, sodium, potassium hydroxide, etc., followed by reaction with acetic anhydride.

Products (6) can be purified by extraction, chromatography or crystallization.

Cyclization of hydroxamates (6) to give β-lactames (7) can be carried out in a suitable organic solvent (for example tetrahydrofuran, acetonitrile of dimethylformamide) preferably by treatment with triphenylphosphine and a dialkyl-azodicarboxylate (such as diethyl- or diisopropyl-azodicarboxylate) or by treatment with triphenylphospine, carbon tetrachloride and triethylamine.

As an alternative, the same conversion can be carried out by converting the alcohol into an alkansulfonyl-derivative by treatment, for example, with methanesulfonylchloride in pyridine, followed by treatment with bases such as $NaHCO_3$ or $Na_2CO_3$ in dipolar solvents such as acetone, dioxane, etc.

Products (7) can be purified by extraction, chromatography or crystallization. The conversion from (7) into (8) can be carried out in various manners, depending on group $R^1$.

For example for $R^1$=benzyl it is possible to carry out a first hydrogenolysis of the 0-benzyl bond with hydrogen at atmospheric pressure or at a higher pressure in the presence of metal catalysts such as for example palladium on carbon, followed by reductive rupture of the N—OH bond to give (8).

The last conversion can be conducted, for example, in a water/alcohol system at a pH ranging from 3 to 10 (preferably equal to 7) by addition of an aqueous solution of titanium trichloride.

For $R^1$=methyl, the abovesaid conversion can be conducted in a single step by means of treatment with alkaline metals (for example sodium) in ammonia, optionally in the presence of organic co-solvents.

For $R^1$=Ac, (7) is converted into the corresponding 1-hydroxyazetidone, by basic hydrolysis in water, alcoholic solvents, or water in the presence of organic co-solvents. The 1-hydroxyazetidone can then be reduced to (8), as already illustrated hereinbefore.

Product (8) can be purified by extraction, chromatography or crystallization. The preferred method for preparing (8) starting from (5) is the one with $R^1$=benzyl.

Compound (8) can be sulfonated with sulfonating agents such as the pyridine-sulfur trioxide complex (to be preferred) or the 2-picolinesulfur trioxide complex, or the dimethyl-formamide-sulfur trioxide complex to form (9) (Y=H).

This sulfonation reaction can be conducted, for example, by treating at 90° C. for 1 hour a solution of (8) in pyridine with 4 equivalents of the pyridine-sulfur trioxide complex.

This product can be isolated as a free acid (by means of chromatography or crystallization) or as tetra-n-butylammonium salt (Y=n.Bu$_4$N) (by extraction from aqueous solutions with suitable organic solvents), or as an inorganic salt or of an organic amine.

Hydrazine (10) [where Y=H, or an inorganic cation (for example Na, Li, K, Mg, Ca) or organic cation (for example trimethylammonium, triethylammonium, tetra-n-bytylammonium)] or a hydrazinium salt thereof (for example chloride, acetate, trifluoroacetate, formiate) is a new product, and as such it is a further object of the present invention. Compound (10) can be obtained from (9) by treatment with a strong carboxylic acid such as e.g. trifluoroacetic or formic acid either in the absence or in the presence of a co-solvent which is suitable for the reaction conditions, such as for example methylene chloride. This reaction can be carried out by stirring, for 1 hour, a solution of (8) in trifluoroacetic acid/methylene chloride 1:1 at temperatures ranging from 0° C. to 25° C.

Zwitterion (11) is obtainable from (10) (or from a hydrazinium salt thereof) by reaction with hydrogen in the presence of crystallization agents such as for example platinum dioxide or Nickel Raney, at pressures from 0 to $2.02 \times 10^5$ Pa and, depending on the catalysts utilized, in water, alcoholic solvents (for example methanol or ethanol) or water-alcoholic solvents mixtures and, last, it is reacted with a proper acylating agent in order to obtain product (1) as desired. The acylation reaction can be conducted in different manners depending on group $R^1$ in position 1.

For $R^1=R'$—CO— ($R'=C_{1-6}$alkyl), $ArCH_2CO$— or $ArOCH_2CO$— (Ar=aryl), crude zwitterion (11) can be reacted with the corresponding acyl chlorides in aprotic solvents such as DMF, acetonitrile, dioxane, in the presence of a tertiary amine (for example $Et_3N$), or in pyridine. For $R^1=$ 2-(2-amino-4-thiazolyl)-2-(Z)-(alkoxyimino)acetyl, the crude zwitterion (11) is treated in an aprotic solvent such as dimethylformamide (DMF), dioxane, or acetonitrile, with a 2-(2-amino-4-triazolyl)-2-(Z) (alkoxyimino)acetic acid, in the presence of 1-hydroxybenzotriazole and of condensing agents such as dicyclohexylcarbodiimide.

EXPERIMENTAL PART

Example 1

(3S,4R)-3-phenoxyacetylamino-4-methyl-2-oxoazetidine-1-sulfonic acid

Compound (1) [where R=$PhOCH_2CO$

Preparation 1: (2S, 3S) 0-benzyl 2-[N,N'-bis-(tert-butyloxycarbonyl)hydrazino]-3-hydroxybutane-hydroxamate (6).

A solution of (5) (9.31 g, 25.7 mmoles) in tetrahydrofuran (100 ml) and water (90 ml) was cooled to 0° C. and treated with aqueous 1N LiOH (56.5 ml). After 45 minutes, the solution was neutralized with 1N HCl and was treated with the chlorohydrate of 0-benzylhydroxylamine (4.92 g, 30.8 mmoles). The pH was adjusted at 4 and a solution of WSC (9.85 9. 51.4 mmoles) in water (100 mi) was added. After 5 minutes, the temperature was allowed to rise to 20° C. and stirring was carried out for 2 hours. The pH was adjusted again at 4 with 1N HCl; the solution was saturated with NaCl, and extracted with diethyl ether. The organic extracts were evaporated and subjected to silica gel chromatography to give 9.03 g of (6) as a colorless foam.

Elemental analysis: C:57.15; H: 7.60; N: 9.40% (calc. for $C_{21}H_{33}N_3O_7$: C: 57.39; H: 7.57; N: 9.56%). $[\alpha]_D = -35.5°$ (c 1.5 $CHCl_3$). $^1$H-NMR (80 MHz, DMSO $d_6$, 90° C.): δ 8.36 [1 H, s broadened NH]; 7.38 [5 H, s, aromatics]; 4.85 [2 H, s, $CH_2Ph$]; 4.30-3.80 [2 H, m, CH—N and CH—OH]; 1.43 and 1.42 [2×9 H, 2, s, $(CH_3)_3C$]; 1.18 [3 H, D, $CH_3.CH$,] 5.9 Hz].

Preparation 2: (3S, 4R) 1-(benzyloxy)-3- [N,N'-bis-(tertbutyloxycarbonyl-hydrazino]-4-methylazetidin-2-one (7).

A solution of hydroxamate (6) (7.88 g, 17.93 mmoles) and of triphenylphosphine (7.05 g, 26.9 mmoles) in tetrahydrofuran (100 ml) was cooled to 0° C. and treated with diethylazodicarboxylate (DEAD) (4.23 ml, 26.9 mmoles). The cooling bath was removed and the solution was stirred for 18 hours. After evaporation of the solvent and silica gel chromatography, 6.81 g of (7) were obtained as a white foam.

Elemental analysis: C: 59.75; H:7.40; N:9.80% Calculated for $C_{21}H_{31}N_3O_6$:C:59.84; H:7.41; N:9.97% $[\alpha]_D$(c 2.75 $CHCl_3$): +7.2°. $^1$H-NMR (80 MHz., $d_6$, DMSO 95° C.): δ 8.79 [1 H, s broadened, NH]; 7.41 [5 H, s, aromatics]; 4.95 [2 H, s, $CH_2$—Ph]; 4.80 [1 H, d, CH—N, J 5.2 Hz]; 3.99 [1 H, dq, CH —$CH_3$, J 5.2 & 6.3 Hz]; 1.43 and 1.42 [2×9 H, 2 s, $(CH_3)_3C$]; 1.18 [3 H, d, $CH_3$—CH, J 6.3 Hz.]; I.R. ($CHCl_3$):$\nu_{max}$ 1774, 1717 $cm^{-1}$.

Preparation 3: (3S, 4R) 3-[N,N'-bis-(tert-butyloxycarbonyl)hydrazino]-4-methylazetidin-2-one (8).

A solution of (7) (7.257 g, 17.22 mmoles) in absolute methanol (70 ml) was hydrogenated for 15 hours on 10% palladium on carbon (400 mg). After the catalyst was filtered off, the colorless solution was evaporated to dryness. The residue was taken up with methanol (20 ml) and was added to a buffer solution (phosphates, 0.2 M) at pH=7 (150 ml). To this suspension there were simultaneously added, under intense stirring, during 30 minutes, a solution of $TiCl_3$ in 2N HCl (27.4 ml, 68.9 mmoles) and an aqueous 3N KOH solution (about 100 ml) in order to maintain the pH value between 6 and 7.5. The suspension was then further stirred for 2 hours and at last it was extracted with ethyl acetate. The organic extracts, after anhydrification and evaporation of the solvent to dryness, were subjected to silica gel chromatography to give 3.740 g (8) as a white solid. M.P.=147°-149° C.

Elemental analysis: C:53.19; H: 7.88; N: 13.08%. Calculated for $C_{14}H_{25}N_3O_5$: C:53.32; H: 7.99; N: 13.32%. $[\alpha]_D$ (c 1.8 $CHCl_3$) = +19.2°. $^1$H-NMR (80 MHz., $d_6$ DMSO, 95° C.) δ 8.81 [1 H, s broadened, NH]; 7.90 [1 H, s broadened, NH]; 4.81 [1 H, dd, CH-N,J 1.4 e 4.9 Hz.(becomes a doublet with J 4.9 Hz. when irradiated at 7.92 ppm)]; 3.71 [1 H, dq, CH—$CH_3$ J 4.9 and 6.3 Hz]; 1,42 [18 H, s, $(CH_3)_3C$]; 1.20 [3 H, d, $CH_3$—CH, J 6.3 Hz.]; I.R. ($CHCl_3$):$\nu_{max}$ 1766,1713 $cm^{-1}$.

Preparation 4: (3S, 4R) 3-[N,N'-bis-(tert-butyloxycarbonyl)hydrazino]-4-methyl-2-oxo-azetidin-1-sulfonic acid (9).

A solution of (8) (1.200 g, 3.805 mmoles) in pyridine (8 ml) was treated with the pyridine-$SO_3$ complex (2.42 g, 15.22 mmoles) and immediately heated to 90° C.

After 1 hour, the mixture was cooled and poured into 1M solution of $KH_2PO_4$ in water. Tetra-n.butylammonium hydroxide (1.356 g, 4.00 mmoles) was added to the solution.

After extraction with methylene chloride and drying the solvent was evaporated; 2.58 g of (9) (Y=n-$Bu_4$ N) were obtained. By silica gel chromatography, 1.438 g of (9) (Y=H) were obtained as a white solid. M.P.>280° C. (a change in the crystal form was observed at 148°-149° C.).

Elemental analysis: C: 42.21, H: 6.49; N: 10.37% calculated for $C_{14}H_{25}N_3O_8S$: C: 42.52; H: 6.37; N: 10.63% $[\alpha]_D$ (c2, $CHCl_3$)= +8.5°. $^1$H-NMR (80 MHz., $d_6$ DMSO, 95° C.): δ8.81 [1 H. s broadened, NH]; 4.78 [1 H, d, CH—N, J 5.4 Hz.]; 3.88 [1 H, q, CH—$CH_3$, J 6.0 Hz.]; 1.43 [18 H, s. $(CH_3)_3C$]; 1.29 [3 H. d, $CH_3$J 6.3 Hz]. I.R. ($CHCl_3$):$\nu_{max}$ 1740 $cm^{-1}$ (broad).

Preparation 5: (3S, 4R) 3-hydrazino-4-methyl-2-oxoazetidin-1-sulfonic acid (10) (as a salt with trifluoroacetic acid). A solution of (9) (372 mg, 0.941 mmoles) in methylene chloride (1-5 ml) was cooled to 0° C. and treated with trifluoro-acetic acid (1.5 ml). After 20 minutes, the cooling bath was removed and the solution was stirred for 50 minutes at room temperature. The solvent was removed at reduced pressure to provide (10) as a white solid (297 mg) (purity, determined by $^1$H-NMR, was 82%). This crude product was suited, without further purifications, to be used for subsequent preparations.

$^1$H-NMR (200 MHz., D$_2$O, 25° C.): δ4.63 [1 H, d, CH—N. J 5.5 Hz.]; 4.41 [1 H, quint., CH—CH$_3$, J 6.2 Hz.]; 1.45 [3 H. d. CH$_3$—CH, J. 6.2 Hz.).

Preparation 6: (3S, 4R) 3- amino-4-methyl-2-oxoazetidin-1 sulfonic acid (11).

A solution of crude (10) prepared as described hereinabove (297 mg) in water (7 ml) was hydrogenated for 18 hours on PtO$_2$ (85 mg). After filtration of the catalyst and evaporation of the solvent to dryness, 249 mg of crude (1) as a white solid were obtained. The purity of (11), determined by means of an internal tracer through $^1$H NMR, was of 36%, corresponding to a yield of 56% from (9). By crystallization or by inverse phase chromatography it was possible to obtain an analytically pure sample, the chemico-physical data of which correspond to those already described (D. M. Floyd, A. W. Fritz, J. Pluscec, E. R. Weaver, C. M. Cimarusti, J. Org. Chem. 1982, 47, 5160).

Preparation 7: (3S, 4R)-3-phenoxyacetyl-amino-4-methyl-2-oxoazetidin-1-sulfonic acid (compound (1) wherein R=Ph-OCH$_2$CO).

As an alternative, the above crude product can be used as such for N-acylation reactions. For example, the reaction with phenoxyacetyl chloride (269 µl) in anhydrous dimethylformamide (2 ml) in the presence of triethylamine (542 µl) carried out at room temperature overnight, followed by treatment, in the order, with a buffer solution at pH=4, and with n-Bu$_4$NHSO$_4$ (658 mg), by extraction with CH$_2$CL$_2$, and by silica gel chromatography, gave 271 mg of the tetra-n-butylammonium salt of 2 (R=PhOCH$_2$) corresponding to a yield of 52% from (9), [α]$_D$= +12.9° (c 2, MeOH). $^1$NMR (200 MHz., CD$_3$OD, 25° C.): δ7.39-6.91 [5 H, m, aromatics]; 5.21 [1 H, d, CH-Nh, J 5.7 Hz.]; 4.61 [2 H. s, OCH$_2$]; 4.25 [1 H, quint., CH —CH$_3$, J, 6.0 Hz.]; 3.40-3.15 [8 H, m, CH$_2$ —N]; 1.76-1.53 [8 H, m, CH$_2$ —CH$_2$ —N]; 1.41 [8 H, sextuplet CH$_2$—CH$_3$, J 7.3 Hz.]; 1.28 [3 H, d, CH$_3$ —CH. J. 6.3 Hz.]; 1.02 [12 H, t, CH$_3$ —CH$_2$ J 7.2 Hz.]. $^{13}$C NMR (50 MHz., CD$_3$OD, 25° C.): δ 171.79 [NH-C=O]; 165.39 [SO$_3$N—C=O]; 159.12 130.60 (2 C), 122.84 and 115.85 (2 C) (aromatics); 68.04 (CH$_2$ —O); 59.47 (CH$_2$ —N); 58.20 and 57.27 (CH—N); 24.81 (CH$_2$—CH$_2$—N); 20.73 (CH$_2$—CH$_3$); 14.20 (CH$_3$CH); 14.26 (CH$_3$—CH$_2$). I.R. (CHC1PV3PV): ν$_{max}$ 1760, 1685.

The product so obtained was salified with a proper acid or base.

We claim:

1. A process for preparing monobactames of formula (1) having the configuration (3S,4R):

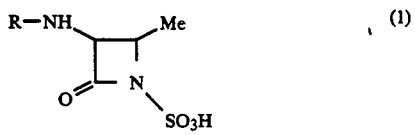

where R=R'—CO—, Ar—CH$_2$CO—, Ar OCH$_2$OCO— and

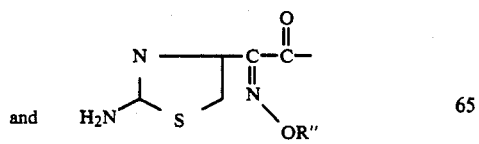

where R=C$_{1-6}$ alkyl

Ar=aryl
and R=C$_{1-6}$alkyl
and their pharmaceutically acceptable salts,
wherein: ethyl hydroxybutanoate of formula (4):

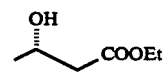

is reacted with di-tert-butylazodicarboxylate (step 1), the resulting product (5)

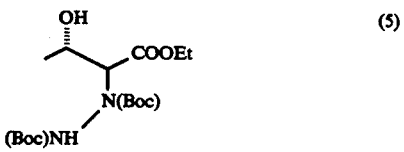

(Boc = tert-butoxycarbonyl)

is hydrolyzed so as to form a free carbonyl in position 1 and is reacted with a hydroxylamine and subsequently with acetic anhydride, or with O-benzyl- or with O-alkyl-hydroxylamine in the presence of a condensing agent, product (6)

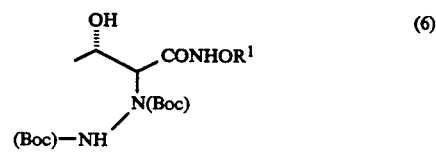

where R$^1$=alkyl, benzyl, or acetyl,
is cyclized to product (7) (step 3), where R$^1$ is defined as above, product (7) is converted into (8) by hydrogenolysis of the N—OH bond (step 4), product (8)

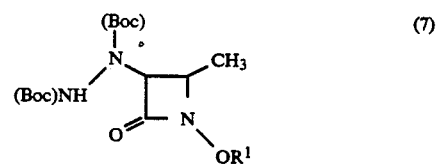

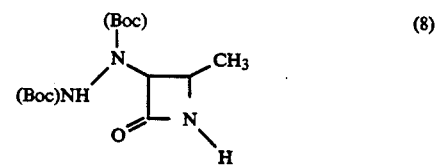

is sulphonated to give acid (9) (Y=H) or a salt thereof (step 5)

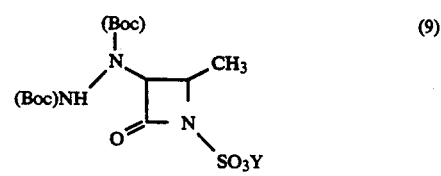

this is converted into the corresponding hydrazine (10) where Y=H or an organic or inorganic cation) or into a salt thereof (by acid treatment) (step 6).

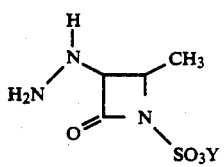

then the hydrazine derivative is catalytically hydrogenated into zwitterion (11) (step 7)

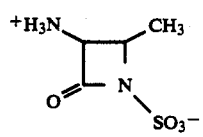

which is finally reacted with an acylating compound in order to give the desired product of formula (1)

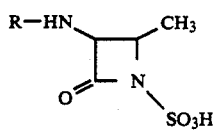

wherein R is as indicated above which can be optionally salified with a base or an acid.

2. The process according to claim 1, wherein step 1 is carried out by converting compound (4) into the corresponding di-anion with lithium diisopropylamide in tetrahydrofuran and by reacting the di-anion with di-tert-butyl-azodicarboxylate at low temperature.

3. The process according to claim 1, wherein for step 2, when $R^1$=benzyl, the condensing agent is 1-(3-diamino-propyl)-3-ethylcarbodiimide and the reaction is conducted at a pH ranging from 4 to 5.

4. The process according to claim 1, wherein for step 2, when $R^1$=acetyl, the reaction is conducted in a basic medium and is followed by reaction with acetic anydride.

5. The process according to claim 1, wherein for step 2, when $R^1$=methyl, the condensing agent is 1-(3-diamino-propyl)-3-ethyl carbodiimide and the reaction is conducted at a PH ranging from 4 to 5.

6. The process according to claim 1, wherein cyclization (step 3) is carried out by treating (6) with triphenylphosphine and diethyl- or diisopropyl-azodicarboxylate in an organic solvent.

7. The process according to claim 1, wherein for step 4, when $R^1$=benzyl, the O-benzyl bond is hydrogenolysed with hydrogen in the presense of catalysts.

8. The process according to claim 1, wherein for step 4, when $R^1$=methyl, the reaction is conducted with alkaline metals in the presence of ammonia.

9. The process according to claim 1, wherein for step 4, when $R^1$=acetyl, compound (7) is converted into the corresponding 1-hydroxyazetidone and then is reduced as in the case where $R^1$=benzyl.

10. The process according to claim 1, wherein the sulfonation (step 5) is carried out with the pyridine-sulphuric anhydride complex.

11. The process according to claim 1, wherein azetidinsulfonic acid (9) is converted into hydrazine (10) (step 6) with trifluoroacetic acid or formic acid.

12. The process according to claim 1, wherein zwitterion (11) is obtained from hydrazine (10) (step 7) by hydrogenation on platinum dioxide or Nickel Raney at a pressure ranging from 0 to $2.02 \times 10^5$ Pa.

13. The process according to claim 1, wherein zwitterion (11) is reacted with phenoxyacetyl chloride or phenylacetyl chloride, or a 2-(2-amino-4-thiazolyl)-2-(Z)-(alkoxyimino) acetic acid in the presence of 1-hydroxy-benzotriazole and dicyclohexylcarbodiimide.

14. The process according to claim 1 wherein Ar is a phenyl group.

* * * * *